United States Patent
Tobinick

(12) 
(10) Patent No.: US 6,537,549 B2
(45) Date of Patent: **\*Mar. 25, 2003**

(54) CYTOKINE ANTAGONISTS FOR THE TREATMENT OF LOCALIZED DISORDERS

(76) Inventor: Edward L. Tobinick, 100 UCLA Medical Plaza, Suite 205, Los Angeles, CA (US) 90024-6903

( * ) Notice: Subject to any disclaimer, the term of this patent is extended or adjusted under 35 U.S.C. 154(b) by 0 days.

This patent is subject to a terminal disclaimer.

(21) Appl. No.: 09/841,844

(22) Filed: Apr. 25, 2001

(65) Prior Publication Data

US 2001/0026801 A1 Oct. 4, 2001

Related U.S. Application Data

(63) Continuation-in-part of application No. 09/826,976, filed on Apr. 5, 2001, now Pat. No. 6,419,944, which is a continuation-in-part of application No. 09/563,651, filed on May 2, 2000, now Pat. No. 6,471,961, which is a continuation-in-part of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.[7] ............................................. A61K 39/42
(52) U.S. Cl. .................... 424/134.1; 424/400; 424/422; 424/427; 424/434; 574/362; 574/363; 574/364
(58) Field of Search .............................. 424/400, 134.1, 424/422, 434, 427; 514/362, 363, 364

(56) References Cited

U.S. PATENT DOCUMENTS

| 5,605,690 A | * | 2/1997 | Jacobs et al. ............. 424/134.1 |
| 5,656,272 A | * | 8/1997 | Le et al. .................. 424/133.1 |
| 6,015,557 A | * | 1/2000 | Tobinick et al. .......... 424/134.1 |
| 6,177,077 B1 | * | 1/2001 | Tobinick et al. .......... 424/134.1 |
| 6,180,355 B1 | * | 1/2001 | Alexander et al. ............ 435/7.1 |

* cited by examiner

Primary Examiner—Thurman K. Page
Assistant Examiner—Lakshmi Channavajjala
(74) Attorney, Agent, or Firm—Ezra Sutton

(57) ABSTRACT

Cytokine antagonists for use in localized clinical disorders are provided for the treatment and prevention of damage to the optic nerve, other cranial nerves, spinal cord, nerve roots, peripheral nerves or muscles caused by any one of the following: a herniated nucleus pulposus, osteoarthritis, other forms of arthritis, disorders of bone, disease, or trauma. The cytokine antagonists are used to treat these disorders by local administration. These cytokine antagonists include antagonists to tumor necrosis factor.

33 Claims, No Drawings

CYTOKINE ANTAGONISTS FOR THE TREATMENT OF LOCALIZED DISORDERS

RELATED APPLICATIONS

This is a continuation-in-part of application Ser. No. 09/826,976, filed on Apr. 5, 2001, now U.S. Pat. No. 6,419,944 which is a continuation-in-part of application Ser. No. 09/563,651, filed on May 2, 2000, was U.S. Pat. No. 6,471,961, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned.

FIELD OF THE INVENTION

The present invention relates to specific cytokine antagonists which are provided for the treatment and prevention of damage to the optic nerve, other cranial nerves, brain, spinal cord, nerve roots, peripheral nerves or muscles caused by any one of the following: a herniated nucleus pulposus, osteoarthritis, other forms of arthritis, disorders of bone, disease, or trauma. More particularly, the cytokine antagonists are used in a new treatment of these disorders utilizing localized anatomic administration which causes inhibition of the action of the corresponding pro-inflammatory cytokine in a localized anatomic area of the human body. The administration of these cytokine antagonists is performed by anatomically localized administration which includes, but is not limited to the following routes: perilesional; intralesional; and transepithelial (for disorders of the optic nerve). Perilesional routes as mentioned above include, but are not limited to, subcutaneous, intramuscular, and epidural routes of administration.

BACKGROUND OF THE INVENTION

Localized administration for the treatment of localized clinical disorders has many clinical advantages over the use of conventional systemic treatment. Locally administered medication after delivery diffuses through local capillary, venous, arterial, and lymphatic action to reach the anatomic site of neurologic or muscular dysfunction; or in the case of the eye through the conjunctiva, then through the aqueous and vitreous humor to reach the optic nerve and retina.

All of the cytokine antagonists which are currently available have been developed for systemic administration. This is because all were developed to treat systemic illnesses, including rheumatoid arthritis, juvenile rheumatoid arthritis, psoriatic arthritis, and Crohn's Disease. Systemic illnesses by definition require systemic treatment.

The use of cytokine antagonists to treat localized disorders is discussed in U.S. Pat. Nos. 6,015,557 and 6,177,077 and other pending applications of the applicant. This invention includes further applications of these ideas.

Localized administration, including perilesional or intralesional administration, when compared to systemic administration, carries with it one or more of the following advantages:

1) greater efficacy due to the achievement of higher local concentration;
2) greater efficacy due to the ability of the administered therapeutic molecule to reach the target tissue without degradation caused by hepatic or systemic circulation;
3) more rapid onset of action;
4) longer duration of action; and
5) Potentially fewer side effects, due to lower required dosage.

Pilot studies conducted by the inventor for one of the disorders discussed herein, herniated nucleus pulposus, have demonstrated the dramatic efficacy, and the extraordinarily rapid onset of action of perilesional administration in this clinical disorder. Ongoing pilot studies for other clinical conditions also demonstrate positive results.

Neurological disorders due to a herniated nucleus pulposus, osteoarthritis, other forms of arthritis, disorders of bone, disease, or trauma causing damage to the optic nerve, other cranial nerves, spinal cord, nerve roots, or peripheral nerves are common and cause considerable morbidity in the general population. Common to all of these disorders is the fact that they can cause permanent neurological damage, that damage can occur rapidly and be irreversible, and that current treatment of these conditions by pharmacologic or other means is often unsatisfactory. Surgical treatment is therefore often required, and is not uniformly successful.

Of these neurological disorders, radiculopathy due to a herniated nucleus pulposus is among the most common. This condition occurs in both the lumbar and cervical regions. Lumbar radiculopathy due to the herniation of a lumbar intervertebral disc causes sciatica i.e. pain in the lower back with radiation to a leg. Neurologic symptoms and signs are often present, including numbness, paresthesia, and motor symptoms involving the leg or foot. Cervical radiculopathy caused by a herniated nucleus pulposus in the cervical region causes pain and neurologic symptoms in the neck and an upper extremity. Other localized neurological conditions include acute spinal cord trauma, spinal cord compression, spinal cord hematoma, cord contusion (these cases are usually traumatic, such as motorcycle accidents or sports injuries); acute or chronic spinal cord compression from cancer (this is usually due to metastases to the spine, such as from prostate, breast or lung cancer); and carpal tunnel syndrome. Localized disorders of the cranial nerves include Bell's Palsy; and glaucoma, caused by glaucomatous degeneration of the optic nerve.

Pharmacologic agents used in the past to treat these disorders have included corticosteroids. Corticosteroid administration, however, may cause multiple side effects, and is often ineffective.

Newer biopharmaceutical medications have been developed which have been shown to offer dramatic clinical benefit for systemic illnesses in humans, even for those disorders which have not responded to large and repeated doses of corticosteroids. These biopharmaceutical medications fall into the category of cytokine antagonists because they block, or antagonize, the biologic action of a specific cytokine which has adverse clinical effects. These cytokines include members of the interleukin class and tumor necrosis factor.

Tumor necrosis factor (TNF) is intimately involved in the nervous system and in inflammatory disorders of muscle. It is central to the response to injury, either virally induced, disease induced, or occurring as a result of mechanical trauma. TNF is also central to neuronal apoptosis, a process important in many neurological disorders.

Specific inhibitors of TNF, only recently commercially available, now provide the possibility of therapeutic intervention in TNF mediated disorders. These agents have been developed to treat systemic illnesses, and therefore have been developed for systemic administration. Various biopharmaceutical companies have developed TNF antagonists to treat systemic illnesses: Immunex Corporation developed etanercept (Enbrel®) to treat rheumatoid arthritis; Johnson and Johnson developed infliximab (Remicade®) to treat Crohn's Disease and rheumatoid arthritis; D2E7, a human anti-TNF monoclonal antibody (Knoll Pharmaceuticals) is being developed to treat rheumatoid arthritis and Crohn's Disease; and Ceiltech is developing CDP 571 to treat Crohn's Disease and CDP 870 to treat rheumatoid arthritis.

Recent research has demonstrated that a new TNF antagonist can be manufactured from an existing molecule by subtracting a portion of the amino acid sequence from the molecule. This has the advantage of making the molecule smaller. This smaller molecule can be easier to manufacture and may have clinical advantages, such as reduced immunogenicity in the human in vivo. Therefore, the molecules of consideration here shall also include, in addition to those specified, any molecule which contains a fragment of any of the named molecules. A fragment shall be defined as an identical amino acid sequence 50% or greater in length of the original molecule and possessing TNF binding capability.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example. U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of specific cytokine antagonists for the suppression and inhibition of the action of IL-1 in the human body to treat neurological disease, trauma, injury or compression, as in the present invention.

U.S. Pat. No. 5,863,769 discloses using IL-1 RA for treating various diseases. However, it does not disclose administering cytokine antagonists locally for the treatment of localized neurological or muscular disorders.

U.S. Pat. No. 6,013,253 discloses using interferon and IL-1 RA for treating multiple sclerosis. However, it does not disclose administering cytokine antagonists locally for the treatment of localized neurological or muscular disorders.

U.S. Pat. No. 5,075,222 discloses the use of IL-1 inhibitors for treatment of various disorders. However, it does not disclose administering cytokine antagonists locally for the treatment of localized neurological or muscular disorders.

PCT Application WO 00/18409 (Apr. 6, 2000) discloses the use of various medications to treat nerve root injury. It does not disclose the methods discussed herein. including localized administration, perilesional administration, or intralesional administration, of the substances discussed herein.

None of the prior art patents disclose or teach the use of localized administration of a cytokine antagonist as in the present invention for suppression and inhibition of the action of a specific cytokine in a human to treat localized neurological or muscular disease, in which the cytokine antagonist provides the patient with a better opportunity to heal, slows disease progression, prevents neurological damage, or otherwise improves the patient's health.

Accordingly, it is an object of the present invention to provide a cytokine antagonist administered through anatomically localized administration as a new method of pharmacologic treatment of neurological disorders, trauma, injuries and compression affecting the nervous system of the human body; and for treating localized disorders of muscle; such that the use of these cytokine antagonists will result in the amelioration of these conditions.

Another object of the present invention is to provide cytokine antagonists for providing suppression and inhibition of the action of specific cytokines in a human to treat neurological injury, trauma or compression; and localized muscular disorders.

Another object of the present invention is to provide cytokine antagonists that reduce inflammation by inhibiting the action of specific cytokines in the human body for the immediate, short term (acute conditions) and long term (chronic conditions), such that this reduction in inflammation will produce clinical improvement in the patient and will give the patient a better opportunity to heal, slow disease progression, prevent neurological damage, prevent muscular damage, or otherwise improve the patient's health.

Another object of the present invention is to provide cytokine antagonists, using anatomically localized administration as the preferred form of administration, that offer acute and chronic treatment regimens for neurological conditions caused by neurological trauma, compression, injury and/or disease, such conditions including acute spinal cord injury; herniated nucleus pulposus (herniated disc); other related neurological disorders and diseases; spinal cord compression due to metastatic cancer; Bell's Palsy; glaucoma and glaucomatous optic nerve degeneration; and muscular disorders.

SUMMARY OF THE INVENTION

The present invention provides a method for inhibiting the action of pro-inflammatory cytokines, including TNF, for treating neurological, optic nerve (glaucoma), and muscular disorders in a human by administering to the human therapeutically effective doses of a specific cytokine antagonist directed against one of the aforementioned cytokines for reducing the inflammation of neuronal, optic nerve, or muscular tissue of the human and/or preventing immune system damage to neuronal tissue (including spinal cord, nerve root, cranial nerve, or peripheral nerve) or muscular tissue. The preferred forms of administration are localized anatomic administration, including perilesional, intralesional, or transepithelial (for disorders of the optic nerve) routes. Perilesional routes as mentioned above include, but are not limited to, subcutaneous, intramuscular, and epidural routes of administration.

DETAILED DESCRIPTION OF THE PREFERRED EMBODIMENTS

Anatomically localized administration is a novel new concept for a delivery method for cytokine antagonists. In this invention it is particularly well matched to the localized clinical disorders being considered.

Some of the clinical conditions being considered here lend themselves to intralesional administration. The most common use of this delivery method is for treating muscle spasm caused by sports injuries, exercise, or trauma. Injection directly into the involved muscle using a small gauge needle is the most efficient way to treat these conditions.

For the great majority of the clinical conditions considered herein, however, perilesional administration is the preferred method of delivery. Perilesional is defined by the Miller-Keane Medical Dictionary, 2000 as "located or occurring around a lesion". The inventor selected this term for use in this invention because it describes the fact that medication need only be delivered to an anatomic area close to the exact area of pathology. The medication in this invention, a cytokine antagonist, then reaches the target tissue by diffusion through surrounding tissue and thereby achieves therapeutic concentration.

One of the advantages of this method of delivery is that administration is simplified. For example, administration for the treatment of a herniated nucleus pulposus producing sciatica is effective by the subcutaneous route in the ipsilateral lumbar region. The subcutaneous route is simple and safe. Hemorrhage due to the use of long or large bore needles is minimized because subcutaneous administration, by the perilesional route, requires only a short, narrow bore needle. Time-consuming and difficult epidural injection is not necessary. Local perilesional administration also has the advantage of providing a depot of therapeutic medication in the surrounding tissue, which will provide therapeutic levels of medication to the treatment site for a prolonged period of time. This decreases the necessity for another injection of medication. Additionally, administering medication locally limits the exposure of the medication to the systemic circulation, thereby decreasing renal and hepatic elimination of the medication, and decreasing exposure of the medication to systemic metabolism. All of these factors tend to increase the therapeutic half-life of the administered cytokine antagonist. Taken together, localized anatomic administration carries with it significant clinical advantages over the various forms of systemic administration previously used with these cytokine antagonists. These forms of systemic administration include the intravenous route; the intramuscular route, when the site of intramuscular administration is remote from the site of pathology; the subcutaneous route, when the site of subcutaneous administration is remote from the site of pathology (such as an abdominal, thigh, or arm administration for the treatment of sciatica); or other methods of administration which rely on the use of the systemic circulation to deliver the medication to the target area of pathology.

For the sake of this invention, perilesional is defined as in anatomic proximity to the site of the pathologic process being treated. This is used generally to indicate that the cytokine antagonist is administered in close enough anatomic proximity to allow the therapeutic molecules to reach the target area of pathology by local diffusion within a reasonably short period of time. In general, for purposes of this invention, to deliver the therapeutic medication by perilesional administration one would attempt to deliver the medication within 10 centimeters of the locus of pathology to allow the medication to reach therapeutic concentration within several hours, and in the best case scenario within minutes.

Cytokine antagonist regimens to be used for the treatment of localized neurological disorders or muscular disorders for the purposes of this patent fall into the general category of TNF antagonists.

TNF antagonists included are the following: etanercept (Enbrel®—Immunex Corporation); infliximab (Remicade®—Johnson and Johnson); D2E7, a human anti-TNF monoclonal antibody (Knoll Pharmaceuticals, Abbott Laboratories); and CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); and a molecule containing at least one soluble TNF receptor.

Trauma, injury, compression and disease can affect individual nerves, nerve roots, the spinal cord, or localized areas of muscle. The disorders which are of most concern and which are included here are the following:

Spinal Cord Injury
Spinal Cord Compression
Herniated Interverterbral Disc (herniated nucleus pulposus)
Glaucoma
Bell's Palsy
Localized Muscular Disorders, including acute muscle pulls, muscle sprains, muscle tears, and muscle spasm.
Alzheimer's Disease
Postherpetic Neuralgia Scientific Background Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel®).

TNF, a naturally occurring cytokine, plays a key role in the inflammatory response, in the immune response, and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

A detailed discussion of each of the clinical conditions follows:

1) Herniated Nucleus Pulposus (Herniated Disc)

Acute low back pain is one of the most common reasons for patients to seek medical care. In the United States over $20 billion is expended annually for the medical treatment of low back pain, and indirect costs, including loss of time from work, are even greater. Sciatica due to a herniated nucleus pulposus is an important cause of acute low back pain. Although many of these patients recover with conservative management, a substantial number need surgery due to neurologic impairment and/or persistent severe pain not responding to medical treatment.

Conservative treatment consists of physical measures, the use of analgesics, muscle relaxants, non-steroidal anti-inflammatory drugs, systemic corticosteroids, or epidural steroid injections. Epidural injections of corticosteroids are commonly used for patients not responding to other methods of treatment, but their true benefit has been questioned (Carette, et. al., NEJM 1997; 336:1634–40.), and despite their continued use many patients still require surgery.

Newer imaging techniques, including computerized axial tomographic (CAT) scans and magnetic resonance imaging (MRI) scans provide non-invasive methods to determine the anatomic extent and location of disc herniation. The medical practitioner can correlate the findings on history and physical examination with the imaging studies and thereby more accurately distinguish sciatica due to herniated nucleus pulposus from other causes of low back pain.

The anatomic basis for sciatica has long been established, but the biochemical basis for the nerve root damage which accompanies disc herniation is less understood. Recent medical research has shed new light on this area. It is now known that the nucleus pulposus contains TNF which causes neuronal damage when it comes into contact with the nerve root.

This new data suggests that nerve root damage from disc herniation is not solely due to mechanical compression, as long thought, but rather is primarily due to direct neurotoxicity from the release of TNF from the herniated disc. Concurrent with these new discoveries regarding the pathogenesis of sciatica are the recent availability of new medications which are specific blockers of TNF.

In accordance with the present invention, localized administration of a cytokine antagonist in this setting includes both of the following routes: 1) epidural; or 2) parenteral injection, to an area anatomically adjacent to the disc herniation. Parenteral injection in this setting includes intramuscular injection or subcutaneous injection. Subcutaneous injection is the simplest and safest method.

Experimental Results

Case 1: Etanercept for the Treatment of Acute Lumbar Radiculopathy

A 44 year old man presented with a three week history of lower back pain which had begun after an episode of heavy lifting. At the onset the pain was present in the lower lumbar area with radiation down the right leg in a sciatic distribution. Three weeks of rest and treatment with oral NSAIDS had failed to result in improvement. Examination revealed the patient to be in acute discomfort. Etanercept 25 mg was administered subcutaneously at the level of the L4-5 interspace, 1.5 cm lateral to the midline, at a depth of 0.5 inch. After an interval of 10 minutes the patient experienced dramatic pain relief. The patient was then able to walk normally, and resumed normal activities. The pain has not recurred for one year.

Case 2: Perilesional Etanercept for the Treatment of Acute Lumbar Radiculopathy Caused by a Herniated Nucleus Pulposus A 34 year old Caucasian male presented with a three week history of acute and severe low back pain radiating into the right lower leg, worsened by movement or by sneezing. The pain was accompanied by right leg paresthesias, and numbness in an S1 distribution. Symptoms had persisted despite two courses of oral methylprednisolone. MRI scan demonstrated a herniated nucleus pulposus at the L5-S1 level, with a protruding disc segment causing compression of the right S1 nerve root. Etanercept was administered in a dose of 25 mg subcutaneously to the lumbar area, at the same level as the disc herniation. It was delivered on the ipsilateral side, approximately 1.5 cm lateral to the spinous process, and injected with a 27 gauge needle at a depth of 0.5 inch. Pain relief was dramatic and rapid, with onset beginning within 10 minutes of administration. Other neurologic symptoms, such as paresthesia, anesthesia, and muscular weakness, also responded dramatically.

Other cytokine antagonists considered here can be used in the same fashion. This particularly includes the TNF antagonists, including infliximab, CDP 870, CDP 571, and D2E7. Although all of these agents were originally designed for systemic administration they can all be administered perilesionally as described above.

2) Acute Spinal Cord Injury

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes.

The emergent use of a cytokine antagonist, delivered by anatomically localized administration, will ameliorate neurological damage caused by acute spinal cord injury. In this setting localized injection can include intrathecal administration; epidural administration; or parenteral injection, either intramuscular or subcutaneous, to an area in close anatomic proximity to the area of spinal cord injury. Anatomically localized injection may be used in conjunction with systemic administration for severe injury. This invention is designed to include the use of cytokine antagonists in the field by paramedical personnel for victims of trauma, such as automobile and motorcycle accidents. It is envisioned that the paramedics will administer a cytokine antagonist, such as etanercept to the victim with known or suspected cord trauma even before they are moved out of the vehicle. This will allow the cytokine antagonist to rapidly act as an anti-inflammatory and neuroprotective agent, helping to ameliorate edema and thereby prevent further neurologic injury.

3) Spinal Cord Compression Due to Metastatic Cancer

Cord compression due to metastatic cancer is a catastrophic event leading to rapid paralysis if not quickly diagnosed and treated. It is most common with cancers of the breast, colon, lung and prostate, but can be a complication of metastatic disease from a wide variety of malignancies, including melanoma and multiple myeloma. Current treatment regimens include high dose steroids, emergency radiation treatment, and/or emergent surgical decompression. Paralysis can occur within hours, so treatment must be initiated within this time period to avoid permanent sequelae.

The emergent use of a cytokine antagonist, delivered by anatomically localized administration, will ameliorate neurological damage in this clinical setting.

4) Bell's Palsy

Bell's palsy is characterized by the sudden onset of hemifacial paralysis caused by acute mononeuropathy of the seventh cranial nerve the facial nerve. It can follow viral infection, vaccination, or may be idiopathic. The mainstay of treatment in the past has been large doses of corticosteroids. In accordance with the present invention, a preferred method would be anatomically localized administration of a specific cytokine antagonist in the region of the facial nerve. For example, etanercept can be administered for Bell's Palsy by subcutaneous injection of 25 mg at the lateral cheek on the ipsilateral side of involvement.

5) Glaucoma

A central feature of glaucoma is pathology of the optic nerve. This is thought to be the key to the pathogenesis of this disorder. Overproduction of inflammatory cytokines, particularly TNF, are centrally involved. In accordance with the present invention, localized administration of a cytokine antagonist by the use of eye drops delivered by the transepithelial route will ameliorate this condition.

6) Localized Muscular Disorders

Inflammation of muscle, caused by trauma, tear, sprain, strain, injury or disease is the result of the release of pro-inflammatory cytokines, particularly TNF. Local administration of a cytokine antagonist results in rapid clinical improvement.

For example, for acute muscle spasm etanercept may be administered into the involved muscle (intralesionally) at a dose of 25 mg, with or without a concurrent dose of local anesthetic, such as Marcaine®.

7) Carpal Tunnel Syndrome

Carpal tunnel syndrome involves compression of the median nerve at the wrist, causing pain and neurologic symptoms in the hand. It is a common condition, being aggravated by repetitive stress injury (RSI) in the workplace (such as typists and writers, manual laborers, etc.), and is also a complication of rheumatoid arthritis (RA). Use of TNF blockade for carpal tunnel syndrome in patients with established RA would likely be covered by the existing arthritis medication for treating RA. But most patients with carpal tunnel syndrome do not have RA; they either have idiopathic CTS or CTS caused by RSI. CTS is a major cause of disability and responds poorly to current treatment regimens, which include NSAIDS, wrist splinting, and injection of steroids.

In accordance with the present invention, local administration of a cytokine antagonist is used to treat this condition. Administration is perilesional by subcutaneous administration in the area immediately overlying the affected median nerve.

8) Alzheimer's Disease

Alzheimer's Disease is a common form of progressive dementia, of unknown cause and without an effective cure. It is characterized by neurofibrillary tangles and plaques on pathologic examination brain tissue.

9) Postherpetic Neuralgia

Patients are considered to have Postherpetic Neuralgia (PHN) if the pain following Zoster persists for greater than one month following healing of the cutaneous eruption. After age 70, PHN occurs in 73% of patients who develop Zoster. Pain lasting more than one year occurs in 48% of patients with PHN over age 70. Pathological changes which have been documented after Zoster can include inflammation, hemorrhagic necrosis, and neuronal loss in the dorsal root ganglion; demyelination, wallerian degeneration and sclerosis of peripheral nerves; acute degeneration of the dorsal horn of the spinal cord, and rarely, unilateral segmental myelitis and leptomeningitis.

Dosages and Routes of Administration

The dosage of a cytokine antagonist used for intralesional or perilesional administration will in general be within one order of magnitude of the dosage used as a single dose for systemic administration. For example, if the usual dose when administered systemically is 100 mg, then the dose used for intralesional therapy will usually be between 10 mg and 100 mg. One exception to this rule is the dose for administration into an anatomically confined structure. In this case, if the structure is small, the dose will need to be reduced accordingly.

For the treatment of acute or severe conditions, the dose will generally be adjusted upward. In the above example the dose selected would therefore be 100 mg, rather than 10 mg, if the condition were acute and/or severe.

Localized perilesional injection can allow the use of subcutaneous administration even in the case when the medication is normally administered intravenously. An example of this would be the use of infliximab subcutaneously to an anatomically adjacent area for the treatment of a herniated nucleus pulposus.

For treating the above diseases with the above mentioned TNF antagonists, these TNF antagonists may be administered by the following routes:

The above TNF antagonists may be administered subcutaneously in the human and the dosage level is in the range of 1 mg to 300 mg per dose, with dosage intervals varying from 1 day to 1 month.

The above TNF antagonists may be administered intramuscularly in the human and the dosage level is in the range of 1 mg to 200 mg per dose, with dosage intervals varying from 1 day to 1 month.

The above TNF antagonists may be administered epidurally in the human and the dosage level is in the range of 1 mg to 300 mg per dose, with dosage intervals varying from 1 day to 2 months.

The above TNF antagonists may be administered transepithelially in the human and the dosage level is in the range of 0.1 mg to 5 mg per dose, with dosage intervals varying from TID to once per month.

ADVANTAGES OF THE PRESENT INVENTION

Accordingly, an advantage of the present invention is that it provides for the localized administration of cytokine antagonists as a new pharmacologic treatment of localized disorders of components of the neurological system, optic nerve, or muscles; such that the use of these cytokine antagonists will result in the amelioration of these conditions.

Another advantage of the present invention is that it provides for cytokine antagonists by anatomically localized administration, which, when compared to systemic administration, produces one or more of the following: greater efficacy; more rapid onset; longer duration of action; or fewer side effects.

Another advantage of the present invention is that it provides for cytokine antagonists for providing suppression and inhibition of the action of cytokines in a human to treat localized neurological injury, trauma, disease, or compression; glaucoma; and muscular diseases.

Another advantage of the present invention is that it provides for cytokine antagonists that reduce inflammation by inhibiting the action of cytokines in the human body for the immediate, short term (acute conditions) and long term (chronic conditions), such that this reduction in inflammation will produce clinical improvement in the patient and will give the patient a better opportunity to heal, slow disease progression, prevent neurological damage, prevent optic nerve and muscular damage, or otherwise improves the patient's health.

Another advantage of the present invention is that it provides for cytokine antagonists, using localized administration, including perilesional or intralesional administration, as the preferred form of administration, for the treatment of localized neurological injury, trauma, disease, or compression; glaucoma; and muscular diseases.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method of treating neurological conditions in a human by inhibiting the action of TNF, by administering a TNF antagonist for reducing the inflammation of neuronal tissue of said human, or for modulating the immune response affecting neuronal tissue of said human, comprising the steps of:
   a) administering a therapeutically effective dosage level to said human of said TNF antagonist selected from the group consisting of a fusion protein identified as etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, and pegylated soluble TNF receptor Type I (PEGs TNF-R1) for reducing the inflammation of neuronal tissue of said human, or for modulating the immune response affecting neuronal tissue of said human; and
   b) administering said dose either intralesionally or perilesionally.

2. A method for inhibiting the action of TNF in accordance with claim 1, wherein the step of administering said dosage level is for treating Alzheimer's Disease.

3. A method for inhibiting the action of TNF in accordance with claim 1, wherein the step of administering said TNF antagonist is performed through any of the following routes: subcutaneous, intrathecal, intramuscular, intranasal, transepidermal, parenteral, transepithelial, or epidural.

4. A method for inhibiting the action of TNF in accordance with claim 1, wherein the step of administering said dosage level is for treating nerve root injury caused by a herniated nucleus pulposus.

5. A method for inhibiting the action of TNF in accordance with claim 1, wherein the step of administering said dosage level is for treating Bell's Palsy.

6. A method for inhibiting the action of TNF in accordance with claim 1, wherein the step of administering said dosage level is for treating Carpal Tunnel Syndrome.

7. A method for inhibiting the action of TNF in accordance with claim 1, wherein the step of administering said dosage level is for treating acute spinal cord injury.

8. A method for inhibiting the action of TNF in accordance with claim 1, wherein the step of administering said dosage level is for treating spinal cord compression.

9. A method for inhibiting the action of TNF in accordance with claim 1, wherein the step of administering said dosage level is for treating spinal stenosis.

10. A method for inhibiting the action of TNF in accordance with claim 1, wherein the step of administering said dosage level is for treating localized disorders of muscle, including muscle spasm, muscle tear, muscle injury, muscle strain, or muscle sprain.

11. A method for inhibiting the action of TNF in accordance with claim 1, wherein the step of administering said dosage level is for treating glaucoma.

12. A method for inhibiting the action of TNF in accordance with claim 1, wherein the step of administering said TNF antagonist is performed subcutaneously in said human wherein said dosage level is in the range of 1 mg to 300 mg per dose.

13. A method for inhibiting the action of TNF in accordance with claim 1, wherein the step of administering said TNF antagonist in the form of etanercept is performed intramuscularly in said human wherein said dosage level is in the range of 1 mg to 100 mg.

14. A method for inhibiting the action of TNF in accordance with claim 1, wherein the step of administering said TNF antagonist in the form of etanercept is performed subcutaneously in said human wherein said dosage level is in the range of 1 mg to 100 mg.

15. A method for inhibiting the action of TNF in accordance with claim 1, wherein the step of administering said TNF antagonist in the form of etanercept is performed subcutaneously in said human wherein said dosage level is in the range of 10 mg to 25 mg.

16. A method for inhibiting the action of TNF in accordance with claim 1, wherein the step of administering said TNF antagonist in the form of D2E7 is performed subcutaneously in said human, wherein said dosage level is in the range of 1 mg to 100 mg.

17. A method for inhibiting the action of TNF in accordance with claim 1, wherein the step of administering said TNF antagonist in the form of D2E7 is performed subcutaneously in said human, wherein said dosage level is in the range of 10 mg to 40 mg.

18. A method of treating or preventing nerve root injury in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:
   a) administering a therapeutically effective dosage level to said human of said TNF antagonist selected from the group consisting of etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, and pegylated soluble TNF receptor Type I (PEGs TNF-R1) for reducing the inflammation of said nerve root of said human, or for modulating the immune response affecting neuronal tissue of said human; and
   b) administering said dose either intralesionally or perilesionally.

19. A method of treating glaucoma in a human by inhibiting the action of TNF, by administering a TNF antagonist for reducing the inflammation of the optic nerve or retina of said human, or for modulating the immune response affecting the optic nerve or retina of said human, comprising the step of:

a) administering a therapeutically effective dosage level to said human of said TNF antagonist selected from the group consisting of etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, and pegylated soluble TNF receptor Type I (PEGs TNF-R1) for treating glaucoma by reducing the inflammation of the optic nerve or retina of said human, or for modulating the immune response affecting the optic nerve or retina of said human.

20. A method for inhibiting the action of TNF in accordance with claim 19, wherein the step of administering said TNF antagonist is performed through any of the following routes: subcutaneous, intranasal, transepidermal, parenteral, or transepithelial.

21. A method of treating neurological conditions in a human by inhibiting the action of TNF, by administering a TNF antagonist for reducing the inflammation of neuronal tissue of said human, or for modulating the immune response affecting neuronal tissue of said human, comprising the step of:

a) administering a therapeutically effective dosage level to said human of said TNF antagonist selected from the group consisting of a fusion protein identified as etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, and pegylated soluble TNF receptor Type I (PEGs TNF-R1) for reducing the inflammation of neuronal tissue of said human, or for modulating the immune response affecting neuronal tissue of said human.

22. A method for inhibiting the action of TNF in accordance with claim 21, wherein the step of administering said dosage level is for treating Alzheimer's Disease.

23. A method for inhibiting the action of TNF in accordance with claim 21, wherein the step of administering said dosage level is for treating glaucoma.

24. A method for inhibiting the action of TNF in accordance with claim 21, wherein the step of administering said dosage level is for treating Postherpetic Neuralgia.

25. A method of treating or preventing nerve root injury in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:

a) administering a therapeutically effective dosage level to said human of a soluble TNF receptor Type I for reducing the inflammation of said nerve root of said human, or for modulating the immune response affecting neuronal tissue of said human; and b) administering said dose perilesionally by subcutaneous administration in the lumbar area (for lumbar or sacral nerve roots) or in the cervical area (for cervical nerve roots).

26. A method of treating or preventing nerve root injury in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:

a) administering a therapeutically effective dosage level to said human of a pegylated soluble TNF receptor Type I for reducing the inflammation of said nerve root of said human, or for modulating the immune response affecting neuronal tissue of said human; and b) administering said dose perilesionally by subcutaneous administration in the lumbar area (for lumbar or sacral nerve roots) or in the cervical area (for cervical nerve roots).

27. A method of treating or preventing nerve root injury in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:

a) administering a therapeutically effective dosage level to said human of a molecule containing at least one soluble TNF receptor for reducing the inflammation of said nerve root of said human, or for modulating the immune response affecting neuronal tissue of said human; and b) administering said dose perilesionally by subcutaneous administration in the lumbar area (for lumbar or sacral nerve roots) or in the cervical area (for cervical nerve roots).

28. A method of treating or preventing nerve root injury in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:

a) administering a therapeutically effective dosage level to said human of said TNF antagonist consisting of a molecule which contains a fragment of any of the molecules selected from the group consisting of etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), soluble TNF receptor Type I, and pegylated soluble TNF receptor Type I (PEGs TNF-R1) for reducing the inflammation of said nerve root of said human, or for modulating the immune response affecting neuronal tissue of said human; and b) administering said dose either intralesionally or perilesionally.

29. A method of treating or preventing nerve root injury caused by a herniated nucleus pulposus in a human by inhibiting the action of TNF, by administering a TNF antagonist for reducing the inflammation of neuronal tissue of said nerve root of said human, or for modulating the immune response affecting neuronal tissue of said nerve root of said human, comprising the steps of:

a) administering a therapeutically effective dosage level to said human of said TNF antagonist selected from the group consisting of etanercept, infliximab, CDP571 (a humanized monoclonal anti-TNF-alpha IgG4 antibody), CDP 870 (a humanized monoclonal anti-TNF-alpha antibody fragment), D2E7 (a human anti-TNF mAb), a molecule containing a soluble TNF receptor, a molecule containing multiple soluble TNF receptors, and a molecule which contains a fragment of any of the above molecules for reducing the inflammation of said nerve root of said human, or for modulating the immune response affecting neuronal tissue of said human; and b) administering said dose either intralesionally or perilesionally.

30. A method of treating a pathologic condition in a human by inhibiting the action of TNF, the pathologic condition being spinal cord compression due to metastatic cancer, by administering a TNF antagonist, defined as any of the following types of molecules directed against said TNF: a monoclonal antibody; a monoclonal antibody fragment; a TNF binding protein; or a fusion protein; comprising the steps of:

a) administering a therapeutically effective dosage level to said human of said TNF antagonist; and b) administering said dose either intralesionally or perilesionally.

31. A method of treating a pathologic condition in a human by inhibiting the action of TNF, the pathologic condition being tumor metastatic to bone, by administering a TNF antagonist, defined as any of the following types of molecules directed against said TNF: a monoclonal antibody; a monoclonal antibody fragment; a TNF binding protein; or a fusion protein; comprising the steps of:

administering a therapeutically effective dosage level to said human of said TNF antagonist; and b) administering said dose either intralesionally or perilesionally.

32. A method of treating a pathologic condition in a human by inhibiting the action of TNF, the pathologic condition being a neurological disease or disorder which is caused or exacerbated by the action of said TNF, by administering a TNF antagonist, defined as any of the following types of molecules directed against said TNF: a monoclonal antibody; a monoclonal antibody fragment; a TNF binding protein; or a fusion protein; comprising the steps of:

a) administering a therapeutically effective dosage level to said human of said TNF antagonist; and b) administering said dose either intralesionally or perilesionally.

33. A method of treating a pathologic condition in a human by inhibiting the action of TNF, the pathologic condition being a malignant tumor, which is caused or exacerbated by the action of said TNF, by administering a TNF antagonist, defined as any of the following types of molecules directed against said TNF: a monoclonal antibody; a monoclonal antibody fragment; a TNF binding protein; or a fusion protein; comprising the steps of:

a) administering a therapeutically effective dosage level to said human of said TNF antagonist; and b) administering said dose either intralesionally or perilesionally.

* * * * *

UNITED STATES PATENT AND TRADEMARK OFFICE
CERTIFICATE OF CORRECTION

| | | |
|---|---|---|
| PATENT NO. | : 6,537,549 B2 | Page 1 of 2 |
| APPLICATION NO. | : 09/841844 | |
| DATED | : March 25, 2003 | |
| INVENTOR(S) | : Edward L. Tobinick | |

It is certified that error appears in the above-identified patent and that said Letters Patent is hereby corrected as shown below:

On the title page item (63), delete the following paragraph:

"Continuation-in-part of application No. 09/826,976, filed on Apr. 5, 2001, now Pat. No. 6,419,944, which is a continuation-in-part of application No. 09/563,651, filed on May 2, 2000, was Pat. No. 6,471,961, which is a continuation-in-part of application No. 09/476,643, filed on Dec. 31, 1999, now Pat No. 6,177,077, which is a continuation-in-part of application No. 09/275,070, filed on March 23, 1999, now Pat No. 6,015,557, which is a continuation-in-part of application No. 09/256,388, filed on Feb. 24, 1999, now abandoned."

and insert therefore:

-- This is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of Serial No. 09/275,070, filed March 23, 1999, now U.S. Pat No. 6,015,557, which is a continuation-in-part of application Ser. No. 09/256,388, filed on Feb. 24, 1999, now abandoned. --

In column 1, lines 5 -15, please delete the following paragraph:

"This is a continuation-in-part of application Ser. No. 09/826,976, filed on Apr. 5, 2001, now U.S. Pat. No. 6,419,944 which is a continuation-in-part of application Ser. No. 09/563,651, filed on May 2, 2000, was U.S. Pat. No. 6,471,961, which is a continuation-in-part of application Ser. No. 09/476,643, filed Dec. 31, 1999, now U.S. Pat No. 6,177,077, which is a continuation-in-part of Serial No. 09/275,070, filed March 23, 1999, now U.S. Pat No. 6,015,557, which is a continuation-in-part of application Ser. No. 09/256,388, filed on Feb. 24, 1999, now abandoned."

and insert therefore:

Signed and Sealed this

Thirteenth Day of July, 2010

David J. Kappos
*Director of the United States Patent and Trademark Office*

-- This is a continuation-in-part of application Ser. No. 09/826,976, filed on Apr. 5, 2001, now US. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of Serial No. 09/275,070, filed March 23, 1999, now U.S. Pat No. 6,015,557, which is a continuation-in-part of application Ser. No. 09/256,388, filed on Feb. 24, 1999, now abandoned. --